US00PP19631P2

(12) United States Plant Patent
Wain

(10) Patent No.: US PP19,631 P2
(45) Date of Patent: Jan. 20, 2009

(54) ***CHRYSANTHEMUM* PLANT NAMED 'YOGIGI GOLD'**

(50) Latin Name: *Chrysanthemum×morifolium*
Varietal Denomination: Yogigi Gold

(75) Inventor: Peter Wain, Southampton (GB)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 12/006,786

(22) Filed: Jan. 3, 2008

(51) Int. Cl.
*A01H 5/00* (2006.01)

(52) U.S. Cl. ..... Plt./295

(58) Field of Classification Search ..... Plt./295
See application file for complete search history.

*Primary Examiner*—Annette H Para
*Assistant Examiner*—S. B. McCormick-Ewoldt
(74) *Attorney, Agent, or Firm*—C. A. Whealy

(57) ABSTRACT

A new and distinct cultivar of *Chrysanthemum* plant named 'Yogigi Gold', characterized by its compact, upright, outwardly spreading and rounded plant habit; freely branching habit; dense and full plant habit; uniform and freely flowering habit; decorative-type inflorescences with obovate-shaped ray florets; golden yellow-colored ray florets; and natural season flowering about September 26$^{th}$ in the Northern Hemisphere.

1 Drawing Sheet

Botanical designation: *Chrysanthemum×morifolium.*
Cultivar denomination: 'Yogigi Gold'.

BACKGROUND OF THE INVENTION

The present invention relates to a new and distinct cultivar of *Chrysanthemum* plant, botanically known as *Chrysanthemum×morifolium,* commercially grown as a garden *Chrysanthemum* and hereinafter referred to by the name 'Yogigi Gold'.

The new *Chrysanthemum* is a naturally-occurring whole plant mutation of the *Chrysanthemum×morifolium* cultivar Yogigi, not patented. The new *Chrysanthemum* was discovered and selected by the Inventor as a single flowering plant from within a population of plants of the cultivar Yogigi in a controlled environment in Alva, Fla. in May, 2005.

Asexual reproduction of the new *Chrysanthemum* by vegetative cuttings was first conducted in Alva, Fla. in July, 2005. Asexual reproduction by cuttings has shown that the unique features of this new *Chrysanthemum* are stable and reproduced true to type in successive generations.

SUMMARY OF THE INVENTION

Plants of the cultivar Yogigi Gold have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yogigi Gold'. These characteristics in combination distinguish 'Yogigi Gold' as a new and distinct garden *Chrysanthemum* cultivar:

1. Compact, upright, outwardly spreading and rounded plant habit.
2. Freely branching habit; dense and full plant habit.
3. Uniform and freely flowering habit.

4. Decorative-type inflorescences with obovate-shaped ray florets.
5. Golden yellow-colored ray florets.
6. Natural season flowering about September 26$^{th}$ in the Northern Hemisphere.

In side-by-side comparisons conducted in Alva, Fla., plants of the new *Chrysanthemum* differed from plants of the parent, the cultivar Yogigi, in the following characteristics:

1. Plants of the new *Chrysanthemum* flower earlier than plants of the cultivar Yogigi.
2. Plants of the new *Chrysanthemum* and the cultivar Yogigi differ in ray floret color as plants of the cultivar Yogigi have light pink-colored ray florets.

Plants of the new *Chrysanthemum* can be compared to plants of the *Chrysanthemum* cultivar Golden Yolynn, disclosed in U.S. Plant Pat. No. 14,721. In side-by-side comparisons conducted in Alva, Fla., plants of the new *Chrysanthemum* differed from plants of the cultivar Golden Yolynn in the following characteristics:

1. Plants of the new *Chrysanthemum* were smaller and more rounded than plants of the cultivar Golden Yolynn.
2. Plants of the new *Chrysanthemum* were more flexible and less brittle than plants of the cultivar Golden Yolynn.
3. Plants of the new *Chrysanthemum* had smaller inflorescences than plants of the cultivar Golden Yolynn.

BRIEF DESCRIPTION OF THE PHOTOGRAPHS

The accompanying photographs illustrate the overall appearance of the new *Chrysanthemum.* The photographs show the colors as true as it is reasonably possible to obtain in colored reproductions of this type. Colors in the photographs may differ slightly from the color values cited in the detailed botanical description which accurately describe the colors of the new *Chrysanthemum.*

The photograph at the bottom of the sheet comprises a side perspective view of a typical flowering plant of 'Yogigi Gold'.

The photograph at the top of the sheet is a close-up view of typical inflorescences of 'Yogigi Gold'.

DETAILED BOTANICAL DESCRIPTION

The aforementioned photographs and following observations and measurements describe plants grown in Alva, Fla. during the late spring and early summer in a polycarbonate-covered greenhouse and under conditions and practices which approximate those generally used in commercial garden *Chrysanthemum* production. During the production of the plants, day temperatures averaged 32° C. and night temperatures averaged 21° C. Plants were grown in containers, exposed to long day/short night conditions and pinched one time. One week after the pinch, the photoinductive short day/long night treatments were started. Plants used in the photographs and for the description were about three months old. In the following description, color references are made to The Royal Horticultural Society Colour Chart, 1995 Edition, except where general terms of ordinary dictionary significance are used.

Botanical classification: *Chrysanthemum×morifolium* cultivar Yogigi Gold.

Parentage: Naturally-occurring whole plant mutation of the *Chrysanthemum×morifolium* cultivar Yogigi, not patented.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Herbaceous decorative-type garden *Chrysanthemum.* Compact, stems upright and outwardly spreading giving a uniformly rounded appearance to the plant. Freely branching habit, about six lateral branches develop after removal of terminal apex (pinching) each with numerous secondary laterals; dense and full plant habit. Moderately vigorous growth habit.

*Plant height.*—About 14.5 cm.

*Plant width.*—About 28 cm.

*Lateral branches.*—Length: About 13 cm. Diameter: About 6 mm. Internode length: About 9 mm. Strength: Strong, flexible. Texture: Pubescent. Color: Close to 147C.

*Leaves.*—Arrangement: Alternate, simple. Length: About 5 cm. Width: About 3.6 cm. Shape: Palmately-lobed; roughly ovate. Apex: Broadly acute and mucronate. Base: Obtuse. Margin: Palmately lobed, sinuses between lateral lobes mostly parallel. Texture, upper and lower surfaces: Fine pubescence; veins prominent on lower surface. Color: Developing and fully expanded foliage, upper surface: 147A; venation, 147B. Developing and fully expanded foliage, lower surface: 147B; venation, 148C. Petiole: Length: About 1.5 cm. Diameter: About 3 mm. Texture, upper and lower surfaces: Pubescent. Color, upper surface: 147B. Color, lower surface: 147D.

Inflorescence description:

*Appearance.*—Decorative-type inflorescence form with obovate-shaped ray florets. Inflorescences borne on terminals above foliage. Disc and ray florets arranged acropetally on a capitulum. Inflorescences fragrant; pungent, herbaceous.

*Flowering response.*—Under natural season conditions, plants flower about September 26$^{th}$ in the Northern Hemisphere. At other times of the year, inflorescence initiation and development can be induced under short day/long night conditions (at least 13.5 hours of darkness). Early flowering habit; plants exposed to photoinductive short day/long night conditions flower about 45 days later.

*Postproduction longevity.*—Plants maintain good color and substance for about four weeks.

*Quantity of inflorescences.*—About 26 inflorescences develop per lateral branch.

*Inflorescence bud.*—Height: About 1.2 cm. Diameter: About 1.3 cm. Shape: Oblate. Color: Close to 13B.

*Inflorescence size.*—Diameter: About 3.7 cm. Depth (height): About 1.4 cm. Disc diameter: About 4 mm. Receptacle diameter: About 1.7 cm. Receptacle height: About 5 mm. Receptacle color: 147B.

*Ray florets.*—Orientation: Initially upright, then about 90° from vertical or perpendicular to peduncle. Length: About 1.8 cm. Width: About 6 mm. Shape: Obovate. Apex: Emarginate. Base: Acute. Margin: Entire. Texture, upper and lower surfaces: Smooth, glabrous, velvety. Number of ray florets per inflorescence: About 134 arranged in about eight whorls. Color: When opening, upper surface: Close to 13B. When opening, lower surface: Close to 13C. Fully opened, upper surface: Close to 12B. Fully opened, lower surface: Close to 12C.

*Disc florets.*—Shape: Tubular, elongated. Length: About 4 mm. Diameter: About 1 mm. Number of disc florets per inflorescence: About 38. Color, immature: Apex: Close to 21A. Mid-section: Close to 17B. Base: Close to 145D. Color, mature: Apex: Close to 17A. Mid-section: Close to 17B. Base: Close to 145D.

*Phyllaries.*—Number of phyllaries per inflorescence: About 20 arranged in about two whorls. Length: About 7 mm. Width: About 2 mm. Shape: Lanceolate. Apex: Acute. Base: Truncate. Texture, upper surface: Smooth, waxy. Texture, lower surface: Pubescent. Color, upper and lower surfaces: Close to 146A.

*Peduncles.*—Length, terminal peduncle: About 2.7 cm. Length, fourth peduncle: About 3.3 cm. Length, seventh peduncle: About 3.8 cm. Diameter, terminal peduncle: About 2 mm. Angle: About 45° to 60° from vertical. Strength: Strong; flexible. Texture: Pubescent; longitudinally ridged. Color: Close to 147B to 147C.

*Reproductive organs.*—Androecium: Stamen number: About five per floret. Filament length: About 1 mm. Filament color: Close to 15C. Anther length: About 1 mm. Anther shape: Narrowly oblong. Anther color: Close to 15A. Pollen amount: None observed. Gynoecium: Pistil length: About 4 mm. Stigma shape:

Bi-parted. Stigma color: Close to 15A. Style length: About 1.5 mm. Style color: Close to 15D. Ovary color: Close to 157D.

*Seed/fruit.*—Seed and fruit production has not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and to tolerate temperatures from about 0° C. to about 38° C.

It is claimed:

1. A new and distinct *Chrysanthemum* plant named 'Yogigi Gold' as illustrated and described.

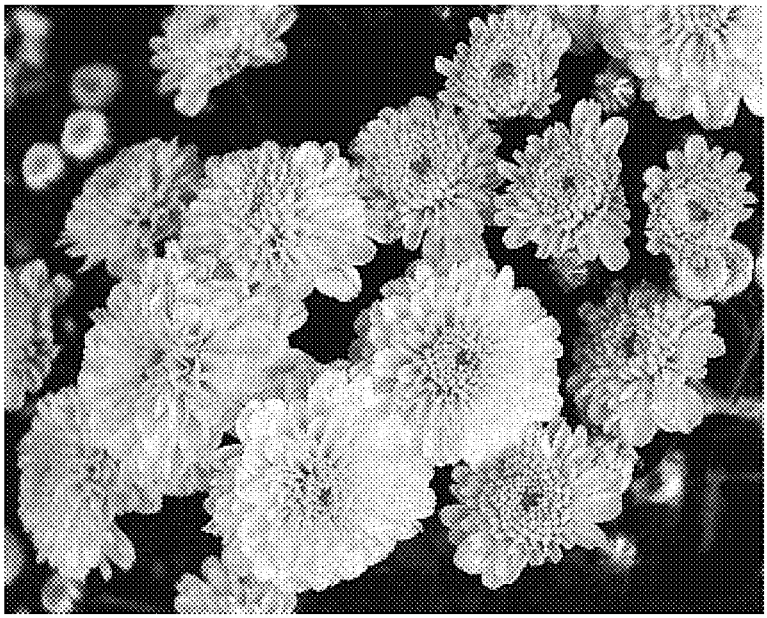
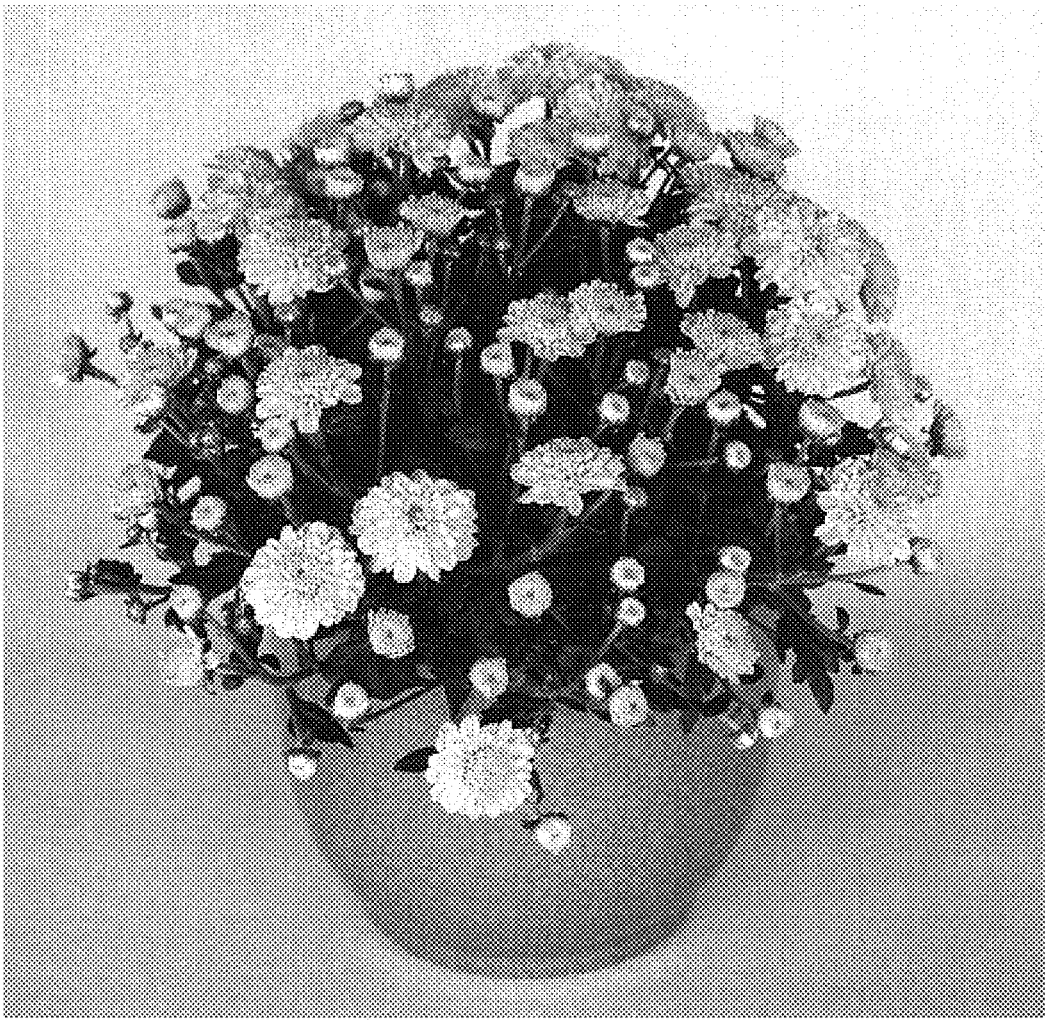

* * * * *